(12) United States Patent
Cheng et al.

(10) Patent No.: US 11,807,908 B2
(45) Date of Patent: Nov. 7, 2023

(54) GENETIC MARKERS USED FOR IDENTIFYING BENIGN AND MALIGNANT PULMONARY MICRO-NODULES AND THE APPLICATION THEREOF

(71) Applicant: Shanghai Biomedical Laboratory, Co., Ltd., Shanghai (CN)

(72) Inventors: Changming Cheng, Shanghai (CN); Chao Yang, Shanghai (CN); Ruiqin Ma, Shanghai (CN); Yin Zhou, Shanghai (CN)

(73) Assignee: Shanghai Biomedical Laboratory Co., Ltd., Shanghai (CN)

( * ) Notice: Subject to any disclaimer, the term of this patent is extended or adjusted under 35 U.S.C. 154(b) by 189 days.

(21) Appl. No.: 16/196,163

(22) Filed: Nov. 20, 2018

(65) Prior Publication Data
US 2019/0078167 A1      Mar. 14, 2019

Related U.S. Application Data

(63) Continuation-in-part of application No. PCT/CN2017/083019, filed on May 4, 2017.

(30) Foreign Application Priority Data

May 25, 2016  (CN) .......................... 201610353398.6
Jun. 25, 2018  (CN) .......................... 201810661113.4

(51) Int. Cl.
| | | |
|---|---|---|
| C12Q 1/6886 | (2018.01) | |
| C12Q 1/6851 | (2018.01) | |
| C12Q 1/6837 | (2018.01) | |
| G16H 50/20 | (2018.01) | |
| G16B 45/00 | (2019.01) | |

(52) U.S. Cl.
CPC ......... *C12Q 1/6886* (2013.01); *C12Q 1/6837* (2013.01); *C12Q 1/6851* (2013.01); *G16B 45/00* (2019.02); *G16H 50/20* (2018.01); *C12Q 2600/106* (2013.01); *C12Q 2600/112* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS 6,582,908 B2 *   6/2003  Fodor ................... B01J 19/0046
                                                                  435/288.3

FOREIGN PATENT DOCUMENTS

| CN | 105368853 A | 3/2016 |
|---|---|---|
| CN | 105368925 A | 3/2016 |
| WO | 2016033163 A1 | 3/2016 |

OTHER PUBLICATIONS

Sanchez-Palencia (Int J Cancer 129 pp. 355-364 2011).*
Pedraza (Cancer 2010; 116: 486-96).*
Yabuki (Cancer Genetics and Cytogenetics 173 (2007) 1-9).*
NEB catalog (1998/1999 pp. 121, 284).*
Rothstein (PNAS 1994 vol. 91 pp. 4155-4159).*
The Mammalian Gene Collection (Mammalian cDNAs (horizondiscovery.com) last updated Mar. 2009 and accessed online Dec. 27, 2022).*
Dong, J., "Part 1 Development and Validation of Clinical Diagnostic Models for the Probability of Malignancy in Solitary Pulmonary Nodules; Part II Application of Non-Small Cell Lung Cancer Biomarker to Monitor Recurrence of Preoperative and Postoperative NSCLC Patient," Medicine & Public Health, China Doctoral Dissertations Full-Text Database, No. 11, E072-40 (Nov. 15, 2014).
International Preliminary Report on Patentability dated Nov. 27, 2018 in International Application No. PCT/CN2017/083019.
International Search Report dated Jul. 26, 2017 in International Application No. PCT/CN2017/083019.
Luo et al., "Diagnostic Value of CEA, NSE, CA125 and CA199 in Solitary Pulmonary Nodules," Journal of Hainan Medical University, vol. 19, No. 1, pp. 107-109 (Nov. 2, 2012) (First Page English Abstract).
Peng et al., "Diagnostic Utility of Serum Tumor Markers in the Solitary Palmonary Nodule," Chinese Journal of Laboratory Diagnosis, vol. 13, No. 3, pp. 359-361 (Mar. 31, 2009) (First Page English Abstract).
Shi et al., "Diagnostic Utility of Serum CEA, Ca199, Ca125 and Cyfra21-1 in the Solitary Palmonary Nodule," The Journal of Practical Medicine, vol. 27, No. 3, pp. 432-434 (Dec. 31, 2011).
Shi et al., "The Value of Serum Tumor Marker in the Diagnosis of Lung Cancer," Chinese Journal of Oncology, vol. 27, No. 5, pp. 299-301 (May 31, 2005) (First Page English Abstract).

* cited by examiner

*Primary Examiner* — Amanda Haney
(74) *Attorney, Agent, or Firm* — Ice Miller LLP

(57) ABSTRACT

Provided is a group of peripheral blood gene markers for screening benign and malignant pulmonary micro-nodules, comprising: gene sequences characterized by micronodular lung carcinoma as shown in SEQ ID NOs. 1-6, wherein the gene sequences exhibit differential expression in the peripheral blood of micronodular lung carcinoma patients and non-micronodular lung carcinoma patients. In addition, also provided is the use of the above-mentioned gene markers in preparing a product for early screening micronodular lung carcinoma. The gene markers of the invention used for early screening micronodular lung carcinoma, have high sensitivity and strong specificity; besides, they take peripheral blood, which is the easiest to collect in clinic, as the test sample. Owing to the noninvasive and simple sampling mode and high inspection compliance, they are especially applicable for the ultra-early screening of lung carcinoma for large-scale population by matching with CT and other imageological examinations, and they have a broad application prospect.

9 Claims, 2 Drawing Sheets
Specification includes a Sequence Listing.

|  | Training set | | | Test set | | | Combined | | |
|---|---|---|---|---|---|---|---|---|---|
|  | LungCa | Control | Benign | LungCa | Control | Benign | LungCa | Control | Benign |
| Positive | 31 | 3 | 4 | 23 | 2 | 7 | 54 | 5 | 11 |
| Negative | 9 | 25 | 12 | 9 | 12 | 11 | 18 | 37 | 23 |
| Count | 40 | 28 | 16 | 32 | 14 | 18 | 72 | 42 | 34 |
| Sensitivity | 78% | | | 72% | | | 75% | | |
| Specificity | | 94% | | | 72% | | | 79% | |
| Accuracy | | 83% | | | 72% | | | 77% | |
| ROC AUC | | 0.92 | | | 0.81 | | | 0.87 | |

| Nodule size (mm) | Patient Count | Positive Prediction | PPV |
|---|---|---|---|
| 6≤8 | 31 | 24 | 77% |
| 8≤s≤10 | 41 | 30 | 73% |
| Total | 72 | 54 | 75% |

| Probeset ID | Gene Symbol | p value | Fold Change (linear) |
|---|---|---|---|
| 224664_at | ANAPC16 | 9.30E-05 | 1.13 |
| 212519_at | UBE2E1 | 8.00E-06 | 1.21 |
| 205633_s_at | ALAS1 | 1.30E-05 | -1.12 |
| 208898_at | ATP6V1D | 1.02E-04 | 1.17 |
| 208610_s_at | SRRM2 | 8.90E-04 | 1.23 |
| 213366_x_at | ATP5C1 | 2.32E-03 | 1.23 |

| Name | AUC | SE | 95%CI |
|---|---|---|---|
| ANAPC16 | 0.725 | 0.0534 | 0.621 to 0.814 |
| UBE2E1 | 0.538 | 0.0611 | 0.430 to 0.644 |
| ALAS1 | 0.717 | 0.0541 | 0.613 to 0.807 |
| ATP6V1D | 0.654 | 0.0578 | 0.546 to 0.751 |
| SRRM2 | 0.663 | 0.0585 | 0.556 to 0.759 |
| ATP5C1 | 0.648 | 0.0582 | 0.540 to 0.746 |
| 6-Gene Panel | 0.92 | 0.0299 | 0.831 to 0.960 |

GENETIC MARKERS USED FOR IDENTIFYING BENIGN AND MALIGNANT PULMONARY MICRO-NODULES AND THE APPLICATION THEREOF

CROSS-REFERENCE TO RELATED APPLICATION

This application is a Continuation-in-Part of International Application No. PCT/CN2017/083019, filed May 4, 2017, which was published in the Chinese language on Nov. 30, 2017, under International Publication No. WO 2017/202185 A1, which claims priority under 35 U.S.C. § 119(b) to Chinese Application No. 201610353398.6, filed May 25, 2016 and Chinese Application No. 201810661113.4, filed Jun. 25, 2018, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 689133-6US", creation date of Nov. 20, 2018, and having a size of 29 KB. The sequence listing submitted via EFS-Web is part of the specification and is herein incorporated by reference in its entirety.

FIELD OF THE INVENTION

The invention relates to the technical field of molecular biology, in particular to a peripheral blood gene marker for screening benign and malignant pulmonary micro-nodules and use thereof.

BACKGROUND OF THE INVENTION

Lung carcinoma is the primary cause for cancer induced death in urban population in China. According to the data of the statistical yearbook by the Ministry of Health in 2011, the mortality rate induced by lung carcinoma in China was 46.46 persons/100,000 persons in 2010, ranking first in the mortality rate induced by malignant tumors, almost equivalent to the total mortality rate induced by liver cancer, gastric cancer and colorectal cancer. The prognosis of lung carcinoma is closely related to the clinical stage of definite diagnosis, wherein, the treatment of ultra-early Stage 0 in situ lung carcinoma has the best therapeutic effect, and the postoperative 5-year survival rate of the patents is as high as 90%; the postoperative 5-year survival rate of patents with Stage Ia lung carcinoma is 61%, while the overall 5-year survival rate for patients at Stages II-IV decreased from 34% to 5% and below. Therefore, the key to improve the cure rate and reduce the mortality of lung carcinoma is early detection, and especially the ultra-early detection of Stage 0 peripheral in situ lung carcinoma is of great value for improving the cure rate of lung carcinoma.

At present, it is a main method for the early screening of lung carcinoma to examine high-risk populations by using low-dose spiral CT (LDCT) and other high-resolution imaging methods. In the large-scale early screening practice of lung carcinoma, a large number of patients with micro-nodules (with the nodule size less than 10 mm) were found, these micro-nodules may be the benign lesions of lung cancer such as inflammation, etc., or may be micronodular lung carcinoma (accounting for about 30%~40%) containing malignant carcinoma cells, of which most of the micronodular lung carcinomas belong to ultra-early peripheral in situ lung carcinoma (tumor TNM Stage 0) and partially Stage Ia lung carcinoma, and good therapeutic results can be achieved in case of early diagnosis. However, it is very difficult to judge benign and malignant pulmonary micro-nodules clinically, it is mainly because that the sizes of micro-nodules are less than 10 mm, it is difficult to perform biopsy and pathological examination by fine needle puncture, and even if PET-CT examination is performed, the obtained results also have very limited diagnostic value. The detection of other lung carcinoma related serum tumor markers, such as carcinoembryonic antigen (CEA), neuron-specific enolase (NSE), squamous cell carcinoma antigen (SCC-Ag), cytokeratin 19-fragment, etc., has certain reference value for the auxiliary diagnosis of middle-stage and advanced lung carcinoma, but it has little value for the diagnosis of ultra-early peripheral in situ lung carcinoma (Stage 0) and Stage Ia lung carcinoma. In addition, conventional tumor serum protein markers usually have low detection sensitivity; for example, CEA and NSE have a sensitivity (positive detection rate) of only about 30% for middle-stage and advanced lung carcinoma, besides, the serum protein markers have poor specificity for lung carcinoma detection, pneumonia and other benign lesions can also cause abnormal concentrations of protein markers, leading to false positive results of detection. Therefore, in order to accurately identify the benign and malignant micro-nodules found in CT imaging and to discover ultra-early micronodular lung carcinoma as early as possible, it is urgent to develop a detection technique and product that can accurately identify benign and malignant micronodules.

Blood is the largest organ of human body, and blood cell is one of the few cell types that can communicate with almost all tissue cells. If the tissues and organs in vivo have some injuries, inflammation, tumor or other malignant diseases, a series of specific changes will occur in the microenvironment around the diseased tissue cells. When blood flows through various tissues and organs, the microenvironment of the diseased tissue cells exchanges information with blood cells, whereas the blood cells will respond directly or indirectly to these changes have the corresponding gene expression changes, and participate in the information transmission and exchange of the immune system and other systems of the whole body. Such gene expression changes of blood cells are much earlier than the obvious physical signs of the body, containing the distinctive gene expression changes of some diseases. Therefore, it is possible to sensitively capture the early molecular information of tumor or malignant diseases in vivo and screen out the distinctive gene expression signals (markers) of the disease by closely monitoring the expression profile of blood cell genes, providing reliable basis for early detection and monitoring of diseases. Moreover, as a simple and noninvasive examination method, the detection of peripheral blood gene expression is easy for the subject to accept with high compliance of examination, and it has great application value for the early screening/diagnosis of malignant tumors.

SUMMARY OF THE INVENTION

In order to solve the technical problem that it is clinically lack of a biological marker for accurately identifying benign and malignant pulmonary micro-nodules, the invention provides a peripheral blood genetic marker for identifying benign and malignant pulmonary micro-nodules, the marker can more accurately identifying malignant micro-nodules to discover ultra-early micronodular lung cancer with higher detection sensitivity and specificity, besides, it is only necessary to collect 2 ml of peripheral venous blood for detection, and owing to the simple detection process, it is especially applicable for the ultra-early screening of lung carcinoma for large-scale population by matching with CT and other imageological examinations.

In order to solve the above technical problem, the invention is realized by the following technical schemes:

On one aspect of the invention, it provides a product comprising multiple polynucleotides or their fragments, the polynucleotides exhibit differential expression in the peripheral blood of micronodular lung carcinoma patients and non-micronodular lung carcinoma patients, and the polynucleotides comprises gene sequences characterized by micronodular lung carcinoma as shown in SEQ ID NO.1~SEQ ID NO.6, namely ATP5C1, ALAS1, ANAPC16, UBE2E1, ATP6V1D and SRRM2.

The non-micronodular lung carcinoma patients contain patients with benign micronodular patients and healthy subjects.

On another aspect of the invention, it provides a composition, comprising a primer and/or a probe used for detecting differential expression of gene in the peripheral blood of micronodular lung carcinoma patients and non-micronodular lung carcinoma patients, and the gene comprises gene sequences characterized by micronodular lung carcinoma as shown in SEQ ID NO.1~SEQ ID NO.6.

On another aspect of the invention, it also provides the application of the above product comprising multiple polynucleotides or their fragments, and it is used for preparing products for identifying, diagnosing or screening ultra-early lung carcinoma.

Preferably, the product for identifying, diagnosing or screening ultra-early lung carcinoma comprises: a product for detecting micronodular lung carcinoma using real-time quantitative PCR, RNA sequencing or gene chip.

The product for identifying, diagnosing or screening ultra-early lung carcinoma using real-time quantitative PCR comprises a primer for specifically amplifying the gene sequence characterized by micronodular lung carcinoma as shown in SEQ ID NO.1~SEQ ID NO.6.

The product for identifying, diagnosing or screening ultra-early lung carcinoma using gene chip comprises: a probe hybrid with the gene sequence characterized by micronodular lung carcinoma as shown in SEQ ID NO.1~SEQ ID NO.6.

On another aspect of the invention, it also provides a detection kit for identifying, diagnosing or screening ultra-early lung cancer, and the kit comprises a primer and/or a probe specifically pertinent to the gene sequence characterized by micronodular lung carcinoma as shown in SEQ ID NO.1~SEQ ID NO.6. The kit also comprises a primer specifically pertinent to the internal control gene GAPDH.

Preferably, the kit also comprises a fluorescent probe specifically binding with PCR amplified fragments or the SYBR Green dye non-specifically binding with PCR amplified fragments.

Preferably, the sequence of the primer comprises nucleotide sequence as shown in SEQ ID NO.7~SEQ ID NO.20 (comprising primers of the internal control gene); the sequence of the fluorescent probe comprises nucleotide sequence as shown in SEQ ID NO.21~SEQ ID NO.27 (comprising probe of the internal control gene).

On another aspect of the invention, it also provides a detection chip for identifying, diagnosing or screening ultra-early lung carcinoma, the chip comprises a probe hybrid with the gene sequence characterized by micronodular lung carcinoma as shown in SEQ ID NO.1~SEQ ID NO.6.

By using the kit or detection chip of the invention, the expressions of the feature gene sequences of micronodular lung carcinoma indicated by SEQ ID NO.1~SEQ ID NO.6 in the peripheral blood of the subjects can be detected, and then the risk value that the micro-nodule of the subject is lung carcinoma can be obtained by inputting the information of expression up-regulation or down-regulation into the micronodular lung carcinoma identifying model, so as to realize the early screening and diagnosis of lung carcinoma.

The genetic markers of the invention can identify benign and malignant pulmonary micro-nodules, and they have higher detection sensitivity and stronger specificity for ultra-early micronodular lung carcinoma; besides, they take peripheral blood, which is the easiest to collect in clinic, as the test sample. Owing to the noninvasive and simple sampling mode and high inspection compliance, it is especially applicable for the ultra-early screening of lung carcinoma for large-scale population to promote the early discovery of lung carcinoma and improve the cure rate of lung carcinoma, and it has a broad application prospect.

BRIEF DESCRIPTION OF THE DRAWINGS

The invention is further explained in details below by combining with the drawings and specific execution modes.

DETAILED DESCRIPTION OF THE INVENTION

Figure 1:
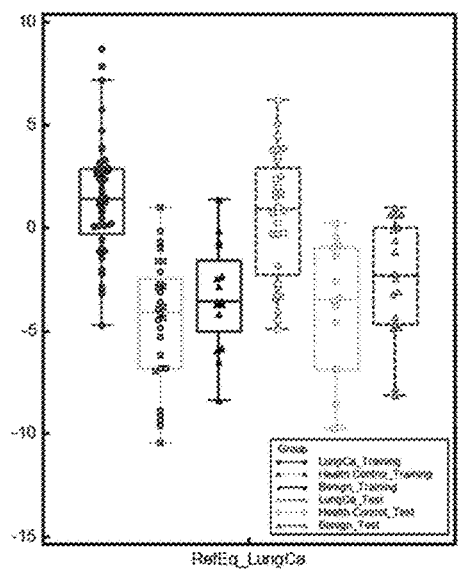
FIG. 1 shows the box-whisker plot for identifying the samples of micronodular lung carcinoma (LungCa), benign pulmonary nodules (Benign) and healthy control (Control) using the combination of 6 feature genes of micronodular lung carcinoma (6-gene Panel) screened by Embodiment 2 of the invention, and the list view for the predictive results of different groups of samples (Training Set and Test Set) and micronodular lung carcinoma of different sizes using the micronodular lung carcinoma identifying model.

Aiming at the technical blank that at present it is difficult to identify benign and malignant pulmonary micro-nodules (with the nodular size less than 10 mm) in clinic, the invention provides a group of peripheral blood gene markers for screening benign and malignant pulmonary micro-nodules by noninvasive sampling mode. Taking the quantitative detection of peripheral blood gene expression profile as the basis, by quantitatively analyzing the differences in the gene expression of total RNA in peripheral blood between micronodular patients (including the patients with benign pulmonary lesions and micronodular lung cancer, with the nodular size less than or equal to 10 mm for all the patients) and healthy subjects without pulmonary lesion, the invention screens out 6 significantly different feature genes (occurring specifical gene expression higher or lower comparing with subjects with pulmonary benign lesion and healthy subjects) of malignant pulmonary micro-nodules (early-stage lung carcinoma) from the peripheral blood gene expression profile based on the logistic regression statistical method, namely gene expression signal of micronodular lung carcinoma feature in the peripheral blood (biological marker), and constructs the corresponding predictive model of micronodular lung carcinoma. Then the relative expressions of the 6 genetic marker of micronodular lung carcinoma in peripheral blood of the subjects are quantitatively detected using fluorescent quantitative PCR, gene expression profile chip or RNA sequencing technology, and benign and malignant pulmonary micro-nodules are identified by combining with the identifying model, so as to identify whether the subject had micronodular lung carcinoma to realize the early discovery of lung carcinoma.

Example 1 Screening of Feature Genetic Marker of Micronodular Lung Carcinoma in Peripheral Blood The screening of feature genes of lung carcinoma comprises the following steps:
1) Collect the peripheral blood samples of 40 malignant mocrinodular patients diagnosed as lung cancer by operation and pathological examination, 16 patients with benign micro-nodules (benign pulmonary lesion) and 28 healthy subjects without pulmonary lesion. The nodular sizes of all the mocrinodular patients were less than or equal to 10 mm by CT examination, and 2-3 ml of peripheral blood was collected for each sample.
2) Extract the total RNA of the above samples using PAXgene Blood RNA Kit, detect the fragment integrity (RIN) of the RNA samples using AgilentBioanalyzer 2100, and detect the purity of the RNA samples using Nano1000 micro ultraviolet spectrophotometer. All the samples must conform to the following conditions for quality control: RNA yield >2 mg, 28S/18S peak ratio >1, RIN value >7, and the 260 nm/280 nm absorbency ratio >1.8.
3) Detect the total RNA samples in the above peripheral blood using Affymetrix Gene Profiling Array U133Plus2chip (human total gene expression profile chip), obtain the data of the peripheral blood gene expression profile of the samples, then perform normalization for the data of the peripheral blood gene expression profile using the MASS method in the AffymetrixExpression Console software, eliminate the system error possibly produced in the detection process of the expression profile chip to obtain the data of peripheral blood gene expression profile for unified comparison.
4) Remove the over-high and over-low gene expression signals in the peripheral blood gene expression profile, choose the genes with moderate expression (with the signal value ranging 100-10000) from all the samples for T test analysis, compare the differences in the gene expression in peripheral blood between the subjects with micronodular lung cancer and the subjects with benign nodules and healthy subjects, and take the genes with the statistical P value <0.05 and the gene expression varying above 1.1 times as the candidate genes for the follow-up analysis.
5) Analyze the correlation between the above candidate genes with micronodular lung cancer, rank them according to the correlation coefficient between the genes and micronodular lung cancer, select a set of gene queue (gene queue I) highly correlated with micronodular lung cancer; furthermore, perform correlation analysis between the remaining genes and the genes in queue I, and select another set of gene queue (gene queue II) highly correlated with gene queue I. Then perform pairwise coupling for the genes in gene queue I and gene queue II to form a series of candidate gene combination.
6) Evaluate the effect of each candidate gene combination in identifying micronodular lung cancer using the logistic regression statistical analysis method, calculate the receiver operator characteristic curve (ROC curve) and area under curve (AUC) of each candidate gene combination, and screen out a series of gene combination having favorable identifying capability for micronodular lung cancer.
7) Verify the screened series of gene combination using real-time fluorescent PCR method, keep the genes having consistent expression changes in the detection using quantitative PCR and gene expression profile chip as the peripheral blood feature genes of micronodular lung cancer, and screen out 6 feature genes of lung cancer, namely ATP5C1, ALAS1, ANAPC16, UBE2E1, ATP6V1D and SRRM2, the gene sequences of the 6 feature genes of lung cancer are as indicated by SEQ ID NO.1~SEQ ID NO.6.
8) Evaluate the diagnostic effect of above 6 gene combinations on micronodular lung cancer using the logistic regression statistical analysis method, calculate the ROC and AUC of the gene combinations, and construct the micronodular lung cancer identifying model as shown below:

$$X = logit(P) = \ln\frac{P}{1-P} = b_0 + b_1\Delta Ct_1 + b_2\Delta Ct_2 + b_3\Delta Ct_3 + b_4\Delta Ct_4 + b_5\Delta Ct_5 + b_6\Delta Ct_6$$

Where, P is the risk value for micronodular lung cancer (malignant pulmonary micro-nodules); $b_0$~$b_6$ are the corresponding parameters of the logistic regression model, respectively; $\Delta Ct_1$~$\Delta Ct_6$ are the differences in the value of quantitative PCR cycles Ct between the 6 genetic markers of micronodular lung cancer and the reference genes; X is the logistic regression log-likelihood ratio.

Example 2 Detection of Micronodular Lung Cancer Using the Screened Feature Genetic Marker of Micronodular Lung Cancer 1. Methods and Steps:
1) Collection of peripheral blood samples of the samples to be detected: Collect the peripheral blood samples of the patients using BD PAXgeneRNA blood collecting vessels (QIAGEN).
2) Extraction and purification of the total RNA in the peripheral blood samples of the samples to be detected: Extract and purify the total RNA in the peripheral blood using the PAXgeneBlood RNA Kit (QIAGEN), and identify the fragment integrity and yield of the extracted total RNA using the Agilent BioAnalyzer 2100 microelectrophoresis analyzer. Detect the purity of the RNA samples using the Nano1000 micro ultraviolet spectrophotometer.
3) Reverse transcription reaction: Use the High-Capacity cDNA Reverse Transcription kit (Life Technology), take the total RNA as the template, and use Olig(dT) as the primer for reverse transcription, and perform reverse transcription to synthetize cDNA.

4) Fluorescent quantitative RT-PCR detection: According to the related sequences of the 6 gene markers (SEQ ID NO.1~SEQ ID NO.6) and the reference gene of GAPDH, design specific primers SEQ ID NO.7~SEQ ID NO.20 (wherein SEQ ID NO.7~SEQ ID NO.8 primers used for specifically amplifying ATP5C1 gene marker as shown in SEQ ID NO.1, SEQ ID NO.9~SEQ ID NO.10 primers used for specifically amplifying ALAS1 gene marker as shown in SEQ ID NO.2, SEQ ID NO.11~SEQ ID NO.12 primers used for specifically amplifying ANAPC16 gene marker as shown in SEQ ID NO.3, SEQ ID NO.13~SEQ ID NO.14 primers used for specifically amplifying UBE2E1 gene marker as shown in SEQ ID NO.4, SEQ ID NO.15~SEQ ID NO.16 primers used for specifically amplifying ATP6V1D gene marker as shown in SEQ ID NO.5, SEQ ID NO.17~SEQ ID NO.18 primers used for specifically amplifying SRRM2 gene marker as shown in SEQ ID NO.6, SEQ ID NO.19~SEQ ID NO.20 primers used for specifically amplifying the reference gene of GAPDH), perform real-time fluorescent quantitative PCR reaction using SEQ ID NO.7~SEQ ID NO.20 as primers, using SEQ ID NO.21~SEQ ID NO.27 as fluorescent probe (wherein SEQ ID NO.21~SEQ ID NO.26 is respectively probe sequence of feature gene sequence as shown in SEQ ID NO.1~SEQ ID NO.6, SEQ ID NO.27 is the probe sequence of reference gene GAPDH), or using the SYBR Green dye which is nonspecific binding with PCR amplified fragment and taking the cDNA obtained by reverse transcription as the template for amplification, use the GAPDH gene as the reference gene, and obtain the relative mRNA content of the 6 genetic markers in the peripheral blood samples. The following Table 1 lists the fluorescent quantitative PCR reaction system.

TABLE 1

Fluorescent Quantitative PCR Reaction System

| Reagent | Concentration | Volume |
|---|---|---|
| Primer for feature genes of micronodular lung cancer | 800 nM | 2 µL |
| Fluorescent probe for feature genes of micronodular lung cancer | 200 nM | 0.5 µL |
| Primer for reference gene of GAPDH | 800 nM | 2 µL |
| Fluorescent probe for reference gene of GAPDH | 200 nM | 0.5 µL |
| 2 × PCR MasterMix | | 12.5 µL |
| cDNA template | 2.67 ng/µL | 7.5 µL |
| Total | | 25 µL |

5) Diagnosis of results of the samples to be detected: According to the relative mRNA contents of the 6 genetic markers of ATP5C1, ALAS1, ANAPC16, UBE2E1, ATP6V1D and SRRM2 in the peripheral blood samples detected by real-time fluorescent quantitative PCR, and calculate the logistic regression log-likelihood ratio of the samples through the micronodular lung cancer identifying model which is constructed in example 1; the detection result with the X value >0 is identified as positive, namely malignant pulmonary micro-nodules (micronodular lung carcinoma); and the detection result with the X value <0 is identified as negative, namely benign pulmonary micro-nodules.

2. Results

Figure 2:
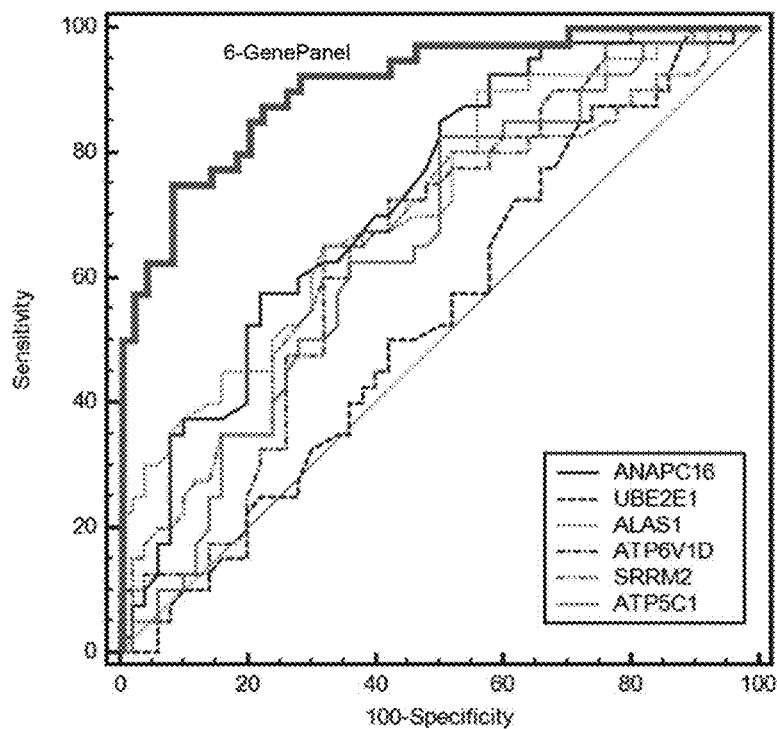
FIG. 2 shows a ROC AUC graph of diagnosing micronodular lung carcinoma by using the screened 6 feature genes of micronodular lung carcinoma and the identifying model in Embodiment 2 of the invention.

The peripheral blood samples were collected from a total of 72 cases of malignant micronodular lung cancer, 42 cases of benign micro-nudules (comprising benign pulmonary lesions such as pneumonia, pulmonary fibrous tissue proliferation etc.) and 34 healthy subjects (Control), the relative expressions of the 6 genetic markers of micronodular lung cancer and the reference gene of GAPDH in peripheral blood were detected using fluorescent quantitative PCR, the logistic regression log-likelihood ratio X value of each sample was calculated, and if the X value is >0, it is considered as positive detection result, otherwise it is considered as negative detection result. By comparing the detection results with the pathological detection results, it is obtained that the feature genetic markers of lung cancer of the invention can better identify malignant micro-nodules (micronodular lung cancer) and benign micro-nodules, it has the sensitivity and specificity both higher than 70% for the detection of micronodular lung cancer, and see FIG. 1-2, table 2-3 for the specific detection results.

TABLE 2

Sensitivity, Specificity and ROC AUC Value for Predicting Malignant Micro-nodules (micronodular lung cancer)

| | Malignant micro-nodules | Benign micro-nodules | Healthy Control |
|---|---|---|---|
| Positive prediction | 54 | 11 | 5 |
| Negative prediction | 18 | 23 | 37 |
| Total | 72 | 34 | 42 |
| Sensitivity | 75% | | |
| Specificity | | | 79% |
| Accuracy | | 77% | |
| ROC AUC Value | | 0.9 | |

TABLE 3

Accuracy of Predicting Malignant Micro-nodules with Different Size

| Nodule size (mm) | Patient Count | Positive Prediction | PPV |
|---|---|---|---|
| d ≤ 5 | 31 | 24 | 77% |
| 5 < d ≤ 10 | 41 | 30 | 73% |
| Total | 72 | 54 | 75% |

The above embodiments only express the execution modes of the invention in more specific and detailed description, but they can't be understood as the limitation to the scope of the invention patent accordingly. It shall be indicated that for the common technicians of this field, under the premise without separating from the concept of the invention, several deformations and improvements can also be obtained, which are all within the protective range of the invention. Therefore, the protective range of the invention patent shall be subject to the claims.

The invention claimed is:

1. A composition comprising first, second, third, fourth, fifth, and sixth combinations, wherein each combination comprises primers and a probe useful for detecting differential expression of genes in the peripheral blood of micronodular lung carcinoma patients and patients without the micronodular lung carcinoma, wherein the genes are (i) HSP90AA1 gene, (ii) UQCRQ gene, (iii) NDUFB2 gene, (iv) RPL24 gene, (v) CKLF gene, and (vi) GLRX gene; wherein
  a) the first combination comprises (i) a first primer comprising the sequence of SEQ ID NO: 13, wherein the first primer can hybridize to HSP90AA1 cDNA and be extended to provide a first polynucleotide; (ii) a second primer comprising the sequence of SEQ ID NO: 14, wherein the second primer can hybridize to the first polynucleotide and be extended to produce a second polynucleotide and (iii) a first probe, wherein the first probe comprises the sequence of SEQ ID NO: 37 and is fluorescently tagged and can hybridize to the second polynucleotide;
  b) the second combination comprises (i) a first primer comprising the sequence of SEQ ID NO: 15, wherein the first primer can hybridize to UQCRQ cDNA and be extended to provide a first polynucleotide; (ii) a second primer comprising the sequence of SEQ ID NO: 16, wherein the second primer can hybridize to the first polynucleotide and be extended to produce a second polynucleotide and (iii) a second probe, wherein the probe can hybridize to the second polynucleotide;
  c) the third combination comprises (i) a first primer comprising the sequence of SEQ ID NO: 23, wherein the first primer can hybridize to NDUFB2 cDNA and be extended to provide a first polynucleotide; (ii) a second primer comprising the sequence of SEQ ID NO: 24, wherein the second primer can hybridize to the first polynucleotide and be extended to produce a second polynucleotide and (iii) a third probe, wherein the probe can hybridize to the second polynucleotide;
  d) the fourth combination comprises (i) a first primer comprising the sequence of SEQ ID NO: 25, wherein the first primer can hybridize to RPL24 cDNA and be extended to provide a first polynucleotide; (ii) a second primer comprising the sequence of SEQ ID NO: 26, wherein the second primer can hybridize to the first polynucleotide and be extended to produce a second polynucleotide and (iii) a fourth probe, wherein the probe can hybridize to the second polynucleotide;
  e) the fifth combination comprises (i) a first primer comprising the sequence of SEQ ID NO: 27, wherein the first primer can hybridize to CKLF cDNA and be extended to provide a first polynucleotide; (ii) a second primer comprising the sequence of SEQ ID NO: 28, wherein the second primer can hybridize to the first polynucleotide and be extended to produce a second polynucleotide and (iii) a fifth probe, wherein the probe can hybridize to the second polynucleotide; and
  f) the sixth combination comprises (i) a first primer comprising the sequence of SEQ ID NO: 35, wherein the first primer can hybridize to GLRX cDNA and be extended to provide a first polynucleotide; (ii) a second primer comprising the sequence of SEQ ID NO: 36, wherein the second primer can hybridize to the first polynucleotide and be extended to produce a second polynucleotide and (iii) a sixth probe, wherein the probe can hybridize to the second polynucleotide.

2. A detection kit for identifying, diagnosing or screening ultra-early lung carcinoma, wherein the kit comprises the combinations of claim 1.

3. The composition of claim 1, wherein the second probe comprises the sequence of SEQ ID NO: 38 and is fluorescently tagged.

4. The composition of claim 1, wherein the third probe comprises the sequence of SEQ ID NO: 42 and is fluorescently tagged.

5. The composition of claim 1, wherein the fourth probe comprises the sequence of SEQ ID NO: 43 and is fluorescently tagged.

6. The composition of claim 1, wherein the fifth probe comprises the sequence of SEQ ID NO: 44 and is fluorescently tagged.

7. The composition of claim 1, wherein the sixth probe comprises the sequence of SEQ ID NO: 48 and is fluorescently tagged.

8. A detection chip for identifying, diagnosing, or screening ultra-early lung carcinoma, comprising primers and probes specific to genes of (i) HSP90AA1 gene, (ii) UQCRQ gene, (iii) NDUFB2 gene, (iv) RPL24 gene, (v) CKLF gene, and (vi) GLRX gene; wherein the primers comprise the polynucleotide sequences of SEQ ID NO:13 to SEQ ID NO:16, SEQ ID NO:23 to SEQ ID NO:28, and SEQ ID NO:35 to SEQ ID NO:36, respectively, and the probes comprise the polynucleotide sequences of SEQ ID NO:37 to SEQ ID NO:38, SEQ ID NO:42 to SEQ ID NO:44, and SEQ ID NO:48, respectively, and the probes are fluorescently tagged.

9. A method for diagnosing lung carcinoma in a subject, comprising:
  (a) collecting a peripheral blood sample from the subject;
  (b) extracting and purifying total RNA from the peripheral blood sample;
  (c) carrying out a reverse transcription reaction on the total RNA;
  (d) performing quantitative RT-PCR detection on the total RNA using the composition of claim 1 to obtain the relative mRNA levels of (i) HSP90AA1, (ii) UQCRQ, (iii) NDUFB2, (iv) RPL24, (v) CKLF, and (vi) GLRX; and
  (e) diagnosing lung carcinoma in the subject when the relative mRNA levels of (i) HSP90AA1, (ii) UQCRQ, (iii) NDUFB2, (iv) RPL24, (v) CKLF, and (vi) GLRX are increased in the peripheral blood sample collected from the subject in comparison to the relative mRNA levels of (i) HSP90AA1, (ii) UQCRQ, (iii) NDUFB2, (iv) RPL24, (v) CKLF, and (vi) GLRX in control samples from subjects that do not have lung carcinoma.

* * * * *

SEQUENCE LISTING

<160> NUMBER OF SEQ ID NOS: 51

<210> SEQ ID NO 1
<211> LENGTH: 1188
<212> TYPE: DNA
<213> ORGANISM: Homo sapiens

<400> SEQUENCE: 1

| | | | | | |
|---|---|---|---|---|---|
| cttgcagaga | aagagtcttt | tgtgcagcac | cctttaaagg | gtgactcgtc | ccacttgtgt | 60 |
| tctctctcct | ggtgcagagt | tgcaagcaag | tttatcggag | tatcgccatg | aagttcgtcc | 120 |
| cctgcctcct | gctggtgacc | ttgtcctgcc | tggggacttt | gggtcaggcc | ccgaggcaaa | 180 |
| agcaaggaag | cactggggag | gaattccatt | tccagactgg | agggagagat | tcctgcacta | 240 |
| tgcgtcccag | cagcttgggg | caaggtgctg | agaagtctg | gcttcgtgtc | gactgccgca | 300 |
| acacagacca | gacctactgg | tgtgagtaca | gggggcagcc | cagcatgtgc | caggctttcg | 360 |
| ctgctgaccc | caaaccttac | tggaatcaag | ccctgcagga | gctgaggcgc | cttcaccatg | 420 |
| cgtgccaggg | ggccccggtg | cttaggccat | ccgtgtgcag | ggaggctgga | ccccaggccc | 480 |
| atatgcagca | ggtgacttcc | agcctcaagg | gcagcccaga | gcccaaccag | cagcctgagg | 540 |
| ctgggacgcc | atctctgagg | cccaaggcca | cagtgaaact | cacagaagca | acacagctgg | 600 |
| gaaaggactc | gatggaagag | ctgggaaaag | ccaaacccac | caccccgaccc | acagccaaac | 660 |
| ctacccagcc | tggacccagg | cccggaggga | atgaggaagc | aaagaagaag | gcctgggaac | 720 |
| attgttggaa | acccttccag | gccctgtgcg | cctttctcat | cagcttcttc | cgagggtgac | 780 |
| aggtgaaaga | ccctacaga | tctgacctct | ccctgacaga | caaccatctc | ttttatatt | 840 |
| atgccgcttt | caatccaacg | ttctcacact | ggaagaagag | agtttctaat | cagatgcaac | 900 |
| ggcccaaatt | cttgatctgc | agcttctctg | aagtttggaa | aagaaacctt | cctttctgga | 960 |
| gtttgcagag | ttcagcaata | tgatagggaa | caggtgctga | tgggcccaag | agtgacaagc | 1020 |
| atacacaact | acttattatc | tgtagaagtt | ttgctttgtt | gatctgagcc | ttctatgaaa | 1080 |
| gtttaaatat | gtaacgcatt | catgaatttc | cagtgttcag | taaatagcag | ctatgtgtgt | 1140 |
| gcaaaataaa | agaatgattt | cagaaatacg | aaaaaaaaaa | aaaaaaaa | | 1188 |

<210> SEQ ID NO 2
<211> LENGTH: 1585
<212> TYPE: DNA
<213> ORGANISM: Homo sapiens

<400> SEQUENCE: 2

| | | | | | |
|---|---|---|---|---|---|
| cttgccggaa | atgacgaacg | agtcaaccgg | atcggtgact | gtggagggcg | agctgagccc | 60 |
| tggccgccgc | cacaatgggc | cgcgagtttg | ggaatctgac | gcggatgcgg | catgtgatca | 120 |
| gctacagctt | gtcaccgttc | gagcagcgcg | cctatccgca | cgtcttcact | aaaggaatcc | 180 |
| ccaatgttct | gcgccgcatt | cgggagtctt | tctttcgcgt | ggtgccgcag | tttgtagtgt | 240 |
| tttatcttat | ctacacatgg | gggactgaag | agttcgagag | atccaagagg | aagaatccag | 300 |
| ctgcctatga | aaatgacaaa | tgagcaacgc | atccggatga | cggttccctg | tctctgaaag | 360 |
| acctttctct | ggaagaggag | tctgcattgt | agtgtctcaa | agacacaata | aacttcctat | 420 |
| ggtctgcact | gttgtgatat | tacatttttg | tgagtagaat | cctgtgtgac | cactaatatt | 480 |
| caagttcatg | aagcgcccct | cctcagcatg | agtcttgaag | ttttgcctgg | tctcgggttt | 540 |
| tggtgaaaga | gcagggctcc | cccttttgttc | cattatctac | aagaaagtag | ctgcaggtac | 600 |
| tcctgcatct | aaccatttgt | gggtgacatg | ggctatggcg | agtgctggtt | cttggccctc | 660 |

| | |
|---|---|
| tgctcccata gcaacaataa agtctactaa ctatattgta attagtatgt gtcagggacg | 720 |
| cttttatttt ttattttttg agatggagtc ttgctctctc acccaggctg gagtgcagtg | 780 |
| gtgtgatctc ggctcactgc catctgtgcc tcctgggttc aaacgattct cctgtctcag | 840 |
| cctccgagta gctgggatta caggtgcagg acaccacacc tggctaattt tttgtatttt | 900 |
| tagtagagac aggtttcacc atgttggcca ggctggtctg gaactcctga cctcagatga | 960 |
| tctgtgcgcc tcagcctccc aaagtgctgg gattacaggc gtaagccatg gtgctctggg | 1020 |
| cctcaaatac tcttcttagc tacacaaatg aactgttaaa cctcacaagc acctttaacg | 1080 |
| tatcctcatt tggcagatga ggaaatgggc acagagagat taagtaattt gccagaaatt | 1140 |
| atacagcagt gaatggtgga gtcttgcact aaagtgatgc tcttaaaact atgctctatt | 1200 |
| gcagggggtgt ccaatctttt agcttccctg ggccacacat aaaatacgct aacattacaa | 1260 |
| tagctgataa gctttaaaaa atggcaaaaa aaaccctcag cgttttagaa agtttacaaa | 1320 |
| tttttgttgg gtcggattca aagccatcct gggctgcttg ctgcccagga ctgcggttgg | 1380 |
| acaagcttgc tctactgcct ttcctcctaa ggcaggcctt agcctgaggg gatatcagct | 1440 |
| ataaaacgga tgaggtgatc tcttagcctc cacagcagtt ttctgtttct gtgccaggag | 1500 |
| gccaacaatg ttttcaacca tatgtggttc ataaagcctc aaagatttac tctggcccttt | 1560 |
| tatgaataaa gtttacccct gatct | 1585 |

<210> SEQ ID NO 3
<211> LENGTH: 708
<212> TYPE: DNA
<213> ORGANISM: Homo sapiens

<400> SEQUENCE: 3

| | |
|---|---|
| agagcggata gagccgtact gccgctctag ttttctttt gctctctatg gttaggagcg | 60 |
| caagcctctc ttcggcccgg aaagatttaa gttcgtgaat gcatacgcaa gactcggagg | 120 |
| tagttccggt tccggcgtgg ccattttcgt tggtggtgtt cagttgtggc ggttgctggt | 180 |
| cagtaacagc caagatgctg cggaatctgc tggctcttcg tcagattggg cagaggacga | 240 |
| taagcactgc ttcccgcagg catttaaaa ataaagttcc ggagaagcaa aaactgttcc | 300 |
| aggaggatga tgaaattcca ctgtatctaa agggtggggt agctgatgcc tcctgtata | 360 |
| gagccaccat gattcttaca gttggtggaa cagcatatgc catatatgag ctggctgtgg | 420 |
| cttcatttcc caagaagcag gagtgacttc agtcatccca gcaatcgctt ggttcagttt | 480 |
| cattcagctc tctatggacc agtaatctga taaataaccg agctcttctt tggggatcaa | 540 |
| tatttattga cttgtagtaa ctgccaccaa taaagcagtc tttaccatgc tttgtctgat | 600 |
| tttatcactt tatgccaata atttcaactt tggtcagcc ttgtaaatct taggtaagga | 660 |
| tcaaagaaat gattcttttg ccactaaact tgtgaaagca aaaaaaaa | 708 |

<210> SEQ ID NO 4
<211> LENGTH: 673
<212> TYPE: DNA
<213> ORGANISM: Homo sapiens

<400> SEQUENCE: 4

| | |
|---|---|
| cttcccggca tccctgcgc gcgcctgcgc gctcggtgac ctttccgagt tggctgcaga | 60 |
| tttgtggtgc gttctgagcc gtctgtcctg cgccaagatg cttcaaagta ttattaaaaa | 120 |
| catatggatc cccatgaagc cctactacac caaagtttac caggagattt ggataggaat | 180 |
| ggggctgatg ggcttcatcg tttataaaat ccgggctgct gataaaagaa gtaaggcttt | 240 |

```
gaaagcttca gcgcctgctc ctggtcatca ctaaccagat ttacttggag tacatgtgaa    300
agaaaacgtc agtctgcctg taaatttcag caagccgtgt tagatgggga gcgtggaacg    360
tcactgtaca cttgtataag taccgtttac ttcatggcat gaataaatgg atctgtgaga    420
tgcactgcta cctggtactg cttttcagtgt gttccccctc agcccctccg gcgtgtcagg    480
catactctga gtagataatt tgtcatgcag cgcatgcaat cagaatctca ctgagccacc    540
catcattgtg aaataattac ctcagttgta caggacttgg tgatcaggat ccaggcactc    600
acttgtattc tactgctcaa taaacgttta ttaaacttga tcctgctact aaaaaaaaa     660 aaaaaaaaaa aaa                                                      673

<210> SEQ ID NO 5
<211> LENGTH: 888
<212> TYPE: DNA
<213> ORGANISM: Homo sapiens

<400> SEQUENCE: 5
atgcgcgcaa gagagcggga agccgagctg ggcgagaagt aggggagggc ggtgctccgc     60
cgcggtggcg gttgctatcg cttcgcagaa cctactcagg cagccagctg agaagagttg    120
agggaaagtg ctgctgctgg gtctgcagac gcgatggata acgtgcagcc gaaaataaaa    180
catcgcccct tctgcttcag tgtgaaaggc cacgtgaaga tgctgcggct ggcactaact    240
gtgacatcta tgaccttttt tatcatcgca caagcccctg aaccatatat tgttatcact    300
ggatttgaag tcaccgttat cttattttc atacttttat atgtactcag acttgatcga    360
ttaatgaagt ggttattttg gcctttgctt gatattatca actcactggt aacaacagta    420
ttcatgctca tcgtatctgt gttggcactg ataccagaaa ccacaacatt gacagttggt    480
ggaggggtgt tgcacttgt gacagcagta tgctgtcttg ccgacggggc ccttatttac    540
cggaagcttc tgttcaatcc cagcggtcct taccagaaaa agcctgtgca tgaaaaaaaa    600
gaagttttgt aattttatat tactttttag tttgatacta agtattaaac atatttctgt    660
attcttccac atattttctg cagttatttt aactcagtat aggagctaga ggaagagatt    720
tccgaagtct gcaccccgcg cagagcacta ctgtaacttc caaggagcg ctgggagcag    780 cgggatcggg ttttccggca cccgggcctg ggtggcaggg aagaatgtgc cgggatccgc    840
ctcagggatc tttgaatctc tttactgcct ggctggccgg cagctccg                888

<210> SEQ ID NO 6
<211> LENGTH: 523
<212> TYPE: DNA
<213> ORGANISM: Homo sapiens

<400> SEQUENCE: 6
ctcctggttc aaaagcagct aaaccaaaag aagcctccag acagccctga gatcacctaa     60
aaagctgcta ccaagacagc cacgaagatc ctaccaaaat gaagcgcttc ctcttcctcc    120
tactcaccat cagcctcctg gttatggtac agatacaaac tggactctca ggacaaaacg    180
acaccagcca aaccagcagc ccctcagcat ccagcaacat aagcggaggc attttccttt    240
tcttcgtggc caatgccata atccaccctct tctgcttcag ttgaggtgac acgtctcagc    300
cttagccctg tgcccctga aacagctgcc accatcactc gcaagagaat cccctccatc    360
tttgggaggg gttgatgcca gacatcacca ggttgtagaa gttgacaggc agtgccatgg    420
gggcaacagc caaaataggg gggtaatgat gtaggggcca agcagtgccc agctgggggt    480
caataaagtt acccttgtac ttgcaaaaaa aaaaaaaaaa aaa                      523
```

<210> SEQ ID NO 7
<211> LENGTH: 509
<212> TYPE: DNA
<213> ORGANISM: Homo sapiens

<400> SEQUENCE: 7

```
cgccggggaa gcgaagtagg caggggcgag gcggctgggg accgcggggc ggacgggagc      60
gagtatgtcc gctctgactc ggctggcgtc tttcgctcgc gttggaggcc gccttttcag     120
aagcggctgc gcacggactg ctggagatgg tggagtccgt catgccggtg gtggtgtgca     180
cattgagccc cggtatagac agttccccca gctgaccaga tcccaggtgt tccagagcga     240
gttcttcagc ggactcatgt ggttctggat tctctggcgc ttttggcatg actcagaaga     300
ggtgctgggt cactttccgt atcctgatcc ttcccagtgg acagatgaag aattaggtat     360
ccctcctgat gatgaagact gaaggtgtag actcagcctc actctgtaca agagccaggt     420
gagaatttca aggattatcg acttcatatt gcacattaaa gttacaaatt aaagtggctt     480
ggtcaagaat gagaaaaaaa aaaaaaaaa                                        509
```

<210> SEQ ID NO 8
<211> LENGTH: 2070
<212> TYPE: DNA
<213> ORGANISM: Homo sapiens

<400> SEQUENCE: 8

```
ctgcaggctc tctccgagag caccaagtcc ttttgctctc catccccgga agacccggct      60
gaaaatccgg aaaaagaatc gggaaacgcc aggaggcata ttgcgcttgc gcacggaggg     120
gccggaagtc gaggcgggag tgactctgct tccgtttctg gttttgctct agtgtttggg     180
tttcttcgcg gctgctcaag atgaaccgac tcttcgggaa agcgaaaccc aaggctccgc     240
cgcccagcct gactgactgc attggcacgg tggacagtag agcagaatcc attgacaaga     300
agatttctcg attggatgct gagctagtga agtataagga tcagatcaag aagatgagag     360
agggtcctgc aaagaatatg gtcaagcaga aagccttgcg agttttaaag caaagagga     420
tgtatgagca gcagcgggac aatcttgccc aacagtcatt caacatggaa caagccaatt     480
ataccatcca gtctttgaag gacaccaaga ccacggttga tgctatgaaa ctgggagtaa     540
aggaaatgaa gaaggcatac aagcaagtga agatcgacca gattgaggat ttacaagacc     600
agctagagga tatgatggaa gatgcaaatg aaatccaaga agcactgagt cgcagttatg     660
gcacccaga actggatgaa gatgatttag aagcagagtt ggatgcacta ggtgatgagc     720
ttctggctga tgaagacagt tcttatttgg atgaggcagc atctgcacct gcaattccag     780
aaggtgttcc cactgataca aaaacaagg atggagttct ggtggatgaa tttggattgc     840
cacagatccc tgcttcatag atttgcatca ttcaagcata tcttgtaaaa caaacacata     900
ttatgggact aggaaatatt tatctttcca aatttgccat aacagattta ggttctcttc     960
ctttctttga aggaaagttt aattacattg ctctttattt ttttccatta agagactcat    1020
tgcttgggaa atgctttctt cgtactaaaa tttgattcct ttttttctta tgaaaaacga    1080
actcagttta aaagtatttt tagctcgtat gacttgtttt cattcattaa taataatttg    1140
aaataaaact aaggaaatgg aatcttaaaa gtctatgaca gtgtaactct acagtctcaa    1200
aatgacctga taaattgata agacaaagat gagattattg gggctgttca tattatgatt    1260
cagaatcatt ttctattgtg gtattatagg ttggttaaag tgatggcctt tttgatgggt    1320
tttgttgtgt cttgtgaaca agtcgttact gtgtccatta ttggaatgga attatcacta    1380
```

-continued

```
ctgtatcatg agtgggtatt ttgattctat ggttccctca gtattacatc ttgacttgta   1440
atcaattatg aatatttctt gatatttaat gtataggaca tttatttata ctcaataaat   1500
atttttcaaa aggatataat tttaataata tcacttcagc ttaaaacctc tactgcggaa   1560
accaaattta atagaatttt aatgtcattt cagcctataa ctccactaca gaaaccaaat   1620
taaccagtag cattgtgagg aaagagcaag gaacaatctg ggcttgggcc ctgggtctac   1680
catttactaa ctactgagta gtctattcaa cctctctaac cttctgtttc cttattagta   1740
aaatcatgct taactcacag agcttttgtg aggaataatt gaggtaatgg tcataagtac   1800
cttgttaact gcaaggggct attcttatat gagggattgt taacaataaa aaagaaactg   1860
cttcattctt ttcttggaag gtgcctggag tactacagca agttcaaact cctgcccaat   1920
ttcagggtct ttaatgatcc tgtcctccct tcctcattca acttgttgcc aacagcatgg   1980
cccctccagc ctagctgggt gcctcacagt gctatgtgca cctgactctc atgtgtctgc   2040
agatcaaacc aataaacatt taggaacacc                                     2070
```

```

<210> SEQ ID NO 9
<211> LENGTH: 1090
<212> TYPE: DNA
<213> ORGANISM: Homo sapiens

<400> SEQUENCE: 9
attgcattcc tgggcattgc taactagtga agtataccag atggaaatgt cttcgaagct     60
gtccctttaa aactcgagca agctaccagg caaactccgc ctccagggag gttccttatt    120
aaataggagc caactggctg ggtcggggct caataccccca agcaatacct gcaactgagg    180
attcttcccg gggagaccgc agcccatcgg catggctcaa gagtttgtga actgcaaaat    240
ccagcctggg aaggtggttg tgttcatcaa gcccacctgc ccgtactgca ggagggccca    300
agagatcctc agtcaattgc ccatcaaaca agggcttctg gaatttgtcg atatcacagc    360
caccaaccac actaacgaga ttcaagatta tttgcaacag ctcacgggag caagaacggt    420
gcctcgagtc tttattggta aagattgtat aggcggatgc agtgatctag tctctttgca    480
acagagtggg gaactgctga cgcggctaaa gcagattgga gctctgcagt aaccacaggt    540
gagtggcaga tctcatagga aatgttcaac aattctgtga aaggtcacag gacccaattg    600
gagaaatcat atgaaaagca tagttggtct tggtgtcata tggatcagag gcacaagtgc    660
agaggctgtg gtcatgcgga acactctgtt atttaagatg gctatccaga taatcctgaa    720
cactgtgtat ttattttatt tagactacca gcaaagatta aagcatgaaa tgtaaaacat    780
ctgataaaac ttacagcccc ctacaccaag agtgtatctg tgaaagagct cctacacttt    840
gaaaacttaa gaatccctta tcatgaagtt tgcctgttct agaattgtaa gattgttaat    900
ttccttcaat ctctagtgac aacacttaat ttcttttcta ataaaaaaaa cctatagatg    960
attcagtgat ttttgtccaa ttcatttgca tgttctcaag acattaagga atgttatgcg   1020
aaatacacta acttaaaact gtgtttatat ttggccctgc cattataaat aaagacacgt   1080
gctgctgtca                                                           1090
```

```

<210> SEQ ID NO 10
<211> LENGTH: 3887
<212> TYPE: DNA
<213> ORGANISM: Homo sapiens

```

```
<400> SEQUENCE: 10
gactgcgcag gcgtgctcac ctggcgtgct ccacccgact gggcgtccgc aggctcctcc         60
cccgggtgtg gcctccgggc ggcatggctg cttcccaggt gatgccggct tcagctagtg        120
gggtctagtt gaccgttccg cagccgccag ggccagcgga aagccggtca gggggaaccg        180
cggcggggct ggtgtcatga gcctgaggtg aacttgaggg tgcctcctca gcggtctccc        240
gccctgccct gaggggcgcc gggacccccaa agagcgagg aagagcgcca ccccgacggc        300
caccgcttcg gagccagcac gcggggtacc ctacggggag cgcggatgcc cccgtgttcg        360
ggcggggacg gctccacccc tcctgggccc tccttcggg acagggactg tcccgcccag        420
agtgctgaat acccgcgcga ccgtctggat ccccgcccag gaagcccctc tgaagcctcc        480
tcgccgccgt ttctgagaag cagggcacct gttaactggt accaagaaaa gcccaagtg         540 tttctctggc atctgatggt gtctggatcc accactctac tctgtctctg gaaacagccc        600
ttccacgtct ctgcattccc tgtcaccgcg tcactggcct tcagacagag ccaaggtgca        660
gggcaacacc tctacaagga tctgcagcca tttatattgc ttaggctact gatgcctgag        720
gaaacccaga cccaagacca accgatggag gaggaggagg ttgagacgtt cgcctttcag        780
gcagaaattg cccagttgat gtcattgatc atcaatactt tctactcgaa caaagagatc        840
tttctgagag agctcatttc aaattcatca gatgcattgg acaaaatccg gtatgaaagc        900
ttgacagatc ccagtaaatt agactctggg aaagagctgc atattaacct tataccgaac        960
aaacaagatc gaactctcac tattgtggat actggaattg gaatgaccaa ggctgacttg       1020
atcaataacc ttggtactat cgccaagtct gggaccaaag cgttcatgga agctttgcag       1080
gctggtgcag atatctctat gattggccag ttcgtgttg gttttttattc tgcttatttg       1140 gttgctgaga agtaactgt gatcaccaaa cataacgatg atgagcagta cgcttgggag       1200
tcctcagcag ggggatcatt cacagtgagg acagacacag gtgaacctat gggtcgtgga       1260
acaaaagtta tcctacacct gaagaagac caaactgagt acttggagga acgaagaata       1320
aaggagattg tgaagaaaca ttctcagttt attggatatc ccattactct ttttgtggag       1380
aaggaacgtg ataaagaagt aagcgatgat gaggctgaag aaaaggaaga caaagaagaa       1440 gaaaagaaa agaagagaa agagtcggaa gacaaacctg aaattgaaga tgttggttct       1500
gatgaggaag aagaaaagaa ggatggtgac aagaagaaga agaagaagat taaggaaaag       1560
tacatcgatc aagaagagct caacaaaaca aagcccatct ggaccagaaa tcccgacgat       1620
attactaatg aggagtacgg agaattctat aagagcttga ccaatgactg ggaagatcac       1680
ttggcagtga agcattttc agttgaagga cagttggaat tcagagccct tctatttgtc       1740
ccacgacgtg ctcccttttga tctgtttgaa aacagaaaga aaaagaacaa catcaaattg       1800
tatgtacgca gagttttcat catggataac tgtgaggagc taatccctga atatctgaac       1860
ttcattagag gggtggtaga ctcggaggat ctccctctaa acatatcccg tgagatgttg       1920
caacaaagca aaattttgaa agttatcagg aagaatttgg tcaaaaaatg cttagaactc       1980
tttactgaac tggcggaaga taaagagaac tacaagaaat tctatgagca gttctctaaa       2040
aacataaagc ttggaataca cgaagactct caaaatcgga agaagctttc agagctgtta       2100
aggtactaca catctgcctc tggtgatgag atggtttctc tcaaggacta ctgcaccaga       2160
atgaaggaga accagaaaca tatctattat atcacaggtg agaccaagga ccaggtagct       2220
aactcagcct ttgtgaacg tcttcggaaa catggcttag aagtgatcta tatgattgag       2280
cccattgatg agtactgtgt ccaacagctg aaggaattg aggggaagac tttagtgtca       2340
```

-continued

| | |
|---|---|
| gtcaccaaag aaggcctgga acttccagag gatgaagaag agaaaaagaa gcaggaagag | 2400 |
| aaaaaaacaa agtttgagaa cctctgcaaa atcatgaaag acatattgga gaaaaaagtt | 2460 |
| gaaaaggtgg ttgtgtcaaa ccgattggtg acatctccat gctgtattgt cacaagcaca | 2520 |
| tatggctgga cagcaaacat ggagagaatc atgaaagctc aagccctaag agacaactca | 2580 |
| acaatgggtt acatggcagc aaagaaacac ctggagataa accctgacca ttccattatt | 2640 |
| gagacccttaa ggcaaaaggc agaggctgat aagaacgaca agtctgtgaa ggatctggtc | 2700 |
| atcttgctttt atgaaactgc gctcctgtct tctggcttca gtctggaaga tccccagaca | 2760 |
| catgctaaca ggatctacag gatgatcaaa cttggtctgg gtattgatga agatgaccct | 2820 |
| actgctgatg ataccagtgc tgctgtaact gaagaaatgc caccccttga aggagatgac | 2880 |
| gacacatcac gcatggaaga agtagactaa tctctggctg agggatgact tacctgttca | 2940 |
| gtactctaca attcctctga taatatattt tcaaggatgt ttttctttat ttttgttaat | 3000 |
| attaaaaagt ctgtatggca tgacaactac tttaagggga agataagatt tctgtctact | 3060 |
| aagtgatgct gtgataccct taggcactaa agcagagctag taatgctttt tgagtttcat | 3120 |
| gttggtttat tttcacagat tggggtaacg tgcactgtaa aacgtatgta acatgatgtt | 3180 |
| aactttgtgg tctaaagtgt ttagctgtca agccggatgc ctaagtagac caaatcttgt | 3240 |
| tattgaagtg ttctgagctg tatcttgatg tttagaaaag tattcgttac atcttgtagg | 3300 |
| atctactttt tgaacttttc attccctgta gttgacaatt ctgcatgtac tagtcctcta | 3360 |
| gaaataggtt aaactgaagc aacttgatgg aaggatctct ccacagggct tgttttccaa | 3420 |
| agaaagtat tgtttggagg agcaaagtta aagcctacc taagcatatc gtaaagctgt | 3480 |
| tcaaaaataa ctcagaccca gtcttgtgga tggaaatgta gtgctcgagt cacattctgc | 3540 |
| ttaaagttgt aacaaataca gatgagttaa aagatattgt gtgacagtgt cttatttagg | 3600 |
| gggaaagggg agtatctgga tgacagttag tgccaaaatg taaaacatga ggcgctagca | 3660 |
| ggagatggtt aaacactagc tgctccaagg gttgacatgg tcttcccagc atgtactcag | 3720 |
| caggtgtggg gtggagcaca cgtaggcaca gaaaacagga atgcagacaa catgcatccc | 3780 |
| ctgcgtccat gagttacatg tgttctctta gtgtccacgt tgttttgatg ttattcatgg | 3840 |
| aataccttct gtgttaaata cagtcactta attccttggc cttaaaa | 3887 |

<210> SEQ ID NO 11
<211> LENGTH: 2373
<212> TYPE: DNA
<213> ORGANISM: Homo sapiens

<400> SEQUENCE: 11

| | |
|---|---|
| cccctccctt agcgggggcg cgcggcgctg aggaccgcac ggaaacgggg aagtcaggtg | 60 |
| gccgctgccg ccgccgccgc cgcggtttgt cgccagaagg aagatggcgg atctggagga | 120 |
| gcagttgtct gatgaagaga aggtgcgtat agcagcaaaa ttcatcattc atgcccctcc | 180 |
| tggagaattt aatgaggttt tcaatgatgt tcggttactg cttaataatg acaatcttct | 240 |
| cagggaagga gcagcccatg catttgcaca gtataacttg gaccagttta ctccagtaaa | 300 |
| aattgaaggt tatgaagatc aggtattgat aacagaacat ggcgacttgg gaatggaaa | 360 |
| gttttttggat ccaaagaaca gaatctgttt taaatttgat cacttaagga aggaggcaac | 420 |
| tgatccaaga ccctgtgaag tagaaaatgc agttgaatca tggagaactt cagtagaaac | 480 |
| tgctctgaga gcttacgtaa aagaacatta cccgaatgga gtctgcactg tgtatggcaa | 540 |
| aaaaatagat ggacagcaaa ccattattgc atgcatagaa agccatcagt tccaagcaaa | 600 |

```
aaattttttgg aatggtcgtt ggaggtcaga atggaagttt acaatcactc cttcaaccac    660
tcaagtggtt ggcatcttga aaattcaggt tcattattat gaagatggta atgttcagct    720
agtgagtcat aaagatatac aagattccct aacagtgtct aatgaagtgc aaacagcaaa    780
agaatttata aagattgtag aagctgcaga aaatgaatac cagactgcca tcagtgagaa    840
ttatcagaca atgtcggaca ctactttcaa agccttacgt cgacagttgc cagttacacg    900
cactaagatt gattggaaca agatcccttag ctacaagatt ggcaaagaga tgcagaatgc    960
ataagatgaa cattgcatga ccggatcatt ttagtgtctt tgcgttaaaa aatcattgca   1020
aaagtattct gaactgtcaa gctgcccagt cagatgggct gttgccattt aaaatcactg   1080
taattaatta gtttgattag agcacaaagc ttagctaatc aaccattatt tttcattttg   1140
tttgttctaa gaggattgaa atcagtttta gtttaaatgt ctttctgtta ggcctttctt   1200
tcttacaatg aagagatgat tcttctagtt tatggttaaa agttttttgaa gtgtctcaaa   1260 aatattttac taactgtaac cctaaaattg atgtcttttg gtttatgaaa tcagtaattt   1320
ttgatatttc cccagttctt tttaatgggg tcaataatgg acattctagt ttaaggtggt   1380
tgatggattt agccatatat gctgctaaag aaattgtcta ccttttcttc ctcacctgtt   1440
ccatttatgt aaagttgaga ttagagggaa agcattttct atatcaattg tgtttaaacc   1500
tttcaagaag gttatttagc tagcttagtg ttgaactaaa ttttttttaa acaaggcaag   1560
gtctaatgct gttttgagat tctgaaatta atgaaaatac ttatttcaga aatgcattta   1620 atgcttttttt tcttgtgaca gttacgcaaa tcagcttgaa ttccatatgt ccctgagtta   1680 ttttttatcat aaagccacaa atgtattata acaaggcaaa ttgtaatata tataatcctg   1740
aactcatgac catgtctcgg tttatttttt ttttcttgga ttgaaaagta ctgaaattca   1800
atgtgacatt aaaatgcaaa ttttcctatt tatttgagta gaaaatcact taccagtgag   1860
catatatatt ttaaaatact ttcttttggat attgtaattc ttaactggtt gtaaattaga   1920
aaagctggga ttacatatgg tgtgcggtta cagtctaaat ttttttcatcc tcctatgcat   1980 cataagcatg tttgtaatat tttcaaaaat agttctactg atgctacagg aatttcaagc   2040
ctgtggtgaa tgttagtatt taccataggg agtgaagtgg agttatggtt tcattcaata   2100
gagtattgct gattatactt gagtggaatc ctttcctcac gtactcccac agacgtctgg   2160
gcctggaaat ttttttttta ttttatttta ttgtttttttt ttttagaaaa acaccacttt   2220
tattatgtac aataaaatat ttcattagct tgaattgtat agattttttaa aaattcaatg   2280 aaagcatgtt gtttaatttc ttttaaaat cactgttggg ctttgaaagc attgagaata   2340
taatatgaaa ttatgaaaaa aaaaaaaaaa aaa                               2373
```

`<210> SEQ ID NO 12`
`<211> LENGTH: 579`
`<212> TYPE: DNA`
`<213> ORGANISM: Homo sapiens`

`<400> SEQUENCE: 12`

```
tctttcttttt cgccatcttt tgtctttccg tggagctgtc gccatgaagg tcgagctgtg     60
cagttttagc gggtacaaga tctacccegg acacggagg cgctacgcca ggaccgacgg    120
gaaggttttc cagtttctta atgcgaaatg cgagtcggct ttcctttcca agaggaatcc    180
tcggcagata aactggactg tcctctacag aaggaagcac aaaaagggac agtcggaaga    240
aattcaaaag aaaagaaccc gccgagcagt caaattccag agggccatta ctggtgcatc    300
tcttgctgat ataatggcca agaggaatca gaaacctgaa gttagaaagg ctcaacgaga    360
```

| | | |
|---|---|---|
| acaagctatc agggctgcta aggaagcaaa aaaggctaag caagcatcta aaaagactgc | | 420 |
| aatggctgct gctaaggcac ctacaaaggc agcacctaag caaaagattg tgaagcctgt | | 480 |
| gaaagtttca gctccccgag ttggtggaaa acgctaaact ggcagattag atttttaaat | | 540 |
| aaagattgga ttataactct agaaaaaaaa aaaaaaaaa | | 579 |

```
<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
```

| | |
|---|---|
| caccagaatg aaggagaacc aga | 23 |

```
<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
```

| | |
|---|---|
| aagacgttcc acaaaggctg ag | 22 |

```
<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
```

| | |
|---|---|
| actaaaggaa tccccaatgt tctg | 24 |

```
<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
```

| | |
|---|---|
| aagataaaac actacaaact gcggc | 25 |

```
<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
```

| | |
|---|---|
| tggtcagtaa cagccaagat gc | 22 |

```
<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
```

| | |
|---|---|
| tatcgtcctc tgcccaatct g | 21 |

```
<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
agaaagccat cagttccaag ca                                              22

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
ccacttgagt ggttgaagga gtg                                             23

<210> SEQ ID NO 21
<211> LENGTH: 24
<212> TYPE: DNA
<213> ORGANISM: Artificial Sequence
<220> FEATURE:
<223> OTHER INFORMATION: primer

<400> SEQUENCE: 21
gaacaagcca attataccat ccag                                            24

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
atgccttctt catttccttt actcc                                           25

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
ttcagcggac tcatgtggtt c                                               21

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
catctgtcca ctgggaagga tc                                              22

<210> SEQ ID NO 25
<211> LENGTH: 23
<212> TYPE: DNA
<213> ORGANISM: Artificial Sequence
<220> FEATURE:
<223> OTHER INFORMATION: primer
```

<400> SEQUENCE: 25
acaatctttt gcttaggtgc tgc                                    23

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
caaaaaaggc taagcaagca tctaa                                  25

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ccgtcggcaa gacagcatac                                        20

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
ggcactgata ccagaaacca caac                                   24

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
gctgcagatt tgtggtgcgt                                        20

<210> SEQ ID NO 30
<211> LENGTH: 23
<212> TYPE: DNA
<213> ORGANISM: Artificial Sequence
<220> FEATURE:
<223> OTHER INFORMATION: primer

<400> SEQUENCE: 30
ggcttcatgg ggatccatat gtt                                    23

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
agaaaaggaa aatgcctccg c                                      21

```
<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32
gcctcctggt tatggtacag ataca                                    25

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gcctgggaac attgttggaa                                          20

<210> SEQ ID NO 34
<211> LENGTH: 24
<212> TYPE: DNA
<213> ORGANISM: Artificial Sequence
<220> FEATURE:
<223> OTHER INFORMATION: primer

<400> SEQUENCE: 34
tcagggagag gtcagatctg tagg                                     24

<210> SEQ ID NO 35
<211> LENGTH: 24
<212> TYPE: DNA
<213> ORGANISM: Artificial Sequence
<220> FEATURE:
<223> OTHER INFORMATION: primer

<400> SEQUENCE: 35
gcatccgcct atacaatctt tacc                                     24

<210> SEQ ID NO 36
<211> LENGTH: 24
<212> TYPE: DNA
<213> ORGANISM: Artificial Sequence
<220> FEATURE:
<223> OTHER INFORMATION: primer

<400> SEQUENCE: 36
caagattatt tgcaacagct cacg                                     24

<210> SEQ ID NO 37
<211> LENGTH: 29
<212> TYPE: DNA
<213> ORGANISM: Artificial Sequence
<220> FEATURE:
<223> OTHER INFORMATION: primer

<400> SEQUENCE: 37
agctacctgg tccttggtct cacctgtga                                29

<210> SEQ ID NO 38
<211> LENGTH: 25
<212> TYPE: DNA
<213> ORGANISM: Artificial Sequence
<220> FEATURE:
<223> OTHER INFORMATION: primer
```

<400> SEQUENCE: 38
ccgcattcgg gagtctttct ttcgc                                                25

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
acgaagagcc agcagattcc gcag                                                 24

<210> SEQ ID NO 40
<211> LENGTH: 27
<212> TYPE: DNA
<213> ORGANISM: Artificial Sequence
<220> FEATURE:
<223> OTHER INFORMATION: primer

<400> SEQUENCE: 40
tccattctga cctccaacga ccattcc                                              27

<210> SEQ ID NO 41
<211> LENGTH: 27
<212> TYPE: DNA
<213> ORGANISM: Artificial Sequence
<220> FEATURE:
<223> OTHER INFORMATION: primer

<400> SEQUENCE: 41
catcaaccgt ggtcttggtg tccttca                                              27

<210> SEQ ID NO 42
<211> LENGTH: 28
<212> TYPE: DNA
<213> ORGANISM: Artificial Sequence
<220> FEATURE:
<223> OTHER INFORMATION: primer

<400> SEQUENCE: 42
aagaggtgct gggtcacttt ccgtatcc                                             28

<210> SEQ ID NO 43
<211> LENGTH: 28
<212> TYPE: DNA
<213> ORGANISM: Artificial Sequence
<220> FEATURE:
<223> OTHER INFORMATION: primer

<400> SEQUENCE: 43
tttgtaggtg ccttagcagc agccattg                                             28

<210> SEQ ID NO 44
<211> LENGTH: 26
<212> TYPE: DNA
<213> ORGANISM: Artificial Sequence
<220> FEATURE:
<223> OTHER INFORMATION: primer

<400> SEQUENCE: 44
ctgtcacaag tgcaaacacc cctcca                                               26

```
<210> SEQ ID NO 45
<211> LENGTH: 22
<212> TYPE: DNA
<213> ORGANISM: Artificial Sequence
<220> FEATURE:
<223> OTHER INFORMATION: primer

<400> SEQUENCE: 45
ctgagccgtc tgtcctgcgc ca                                              22

<210> SEQ ID NO 46
<211> LENGTH: 23
<212> TYPE: DNA
<213> ORGANISM: Artificial Sequence
<220> FEATURE:
<223> OTHER INFORMATION: primer

<400> SEQUENCE: 46
ctgaggggct gctggtttgg ctg                                             23

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
cccttccagg ccctgtgcgc                                                 20

<210> SEQ ID NO 48
<211> LENGTH: 23
<212> TYPE: DNA
<213> ORGANISM: Artificial Sequence
<220> FEATURE:
<223> OTHER INFORMATION: primer

<400> SEQUENCE: 48
ctcgaggcac cgttcttgct ccc                                             23

<210> SEQ ID NO 49
<211> LENGTH: 24
<212> TYPE: DNA
<213> ORGANISM: Artificial Sequence
<220> FEATURE:
<223> OTHER INFORMATION: primer

<400> SEQUENCE: 49
accatgagaa gtatgacaac agcc                                            24

<210> SEQ ID NO 50
<211> LENGTH: 23
<212> TYPE: DNA
<213> ORGANISM: Artificial Sequence
<220> FEATURE:
<223> OTHER INFORMATION: primer

<400> SEQUENCE: 50
cacgatacca aagttgtcat gga                                             23

<210> SEQ ID NO 51
<211> LENGTH: 23
<212> TYPE: DNA
<213> ORGANISM: Artificial Sequence
<220> FEATURE:
<223> OTHER INFORMATION: primer
```

```
<400> SEQUENCE: 51
tcagcaatgc ctcctgcacc acc                                              23
```